(12) United States Patent
Huang et al.

(10) Patent No.: US 9,101,134 B2
(45) Date of Patent: Aug. 11, 2015

(54) COLOR CHANGE SURGICAL PREP SOLUTION

(75) Inventors: Yeong H. Huang, Grayslake, IL (US); Nancy Barot, Mundelein, IL (US)

(73) Assignee: CAREFUSION 2200, INC., San Diego, CA (US)

( * ) Notice: Subject to any disclaimer, the term of this patent is extended or adjusted under 35 U.S.C. 154(b) by 417 days.

(21) Appl. No.: 12/693,262

(22) Filed: Jan. 25, 2010

(65) Prior Publication Data

US 2010/0221193 A1   Sep. 2, 2010

Related U.S. Application Data

(62) Division of application No. 11/542,791, filed on Oct. 3, 2006, now abandoned.

(51) Int. Cl.
| | | |
|---|---|---|
| A61K 49/00 | (2006.01) |
| A01N 37/36 | (2006.01) |
| A01N 31/02 | (2006.01) |
| A01N 31/08 | (2006.01) |
| A01N 31/12 | (2006.01) |
| A01N 31/16 | (2006.01) |
| A01N 47/44 | (2006.01) |
| A01N 59/12 | (2006.01) |
| A61L 27/34 | (2006.01) |
| A61L 27/50 | (2006.01) |
| A61L 27/54 | (2006.01) |

(52) U.S. Cl.
CPC ............... *A01N 37/36* (2013.01); *A01N 31/02* (2013.01); *A01N 31/08* (2013.01); *A01N 31/12* (2013.01); *A01N 31/16* (2013.01); *A01N 47/44* (2013.01); *A01N 59/12* (2013.01); *A61L 27/34* (2013.01); *A61L 27/50* (2013.01); *A61L 27/54* (2013.01); *A61L 2300/404* (2013.01); *A61L 2300/606* (2013.01)

(58) Field of Classification Search
CPC ...................................................... A61K 49/00
USPC .............. 424/70.1, 78.36, 78.37, 401, 59, 60, 424/70.02, 70.03, 400, 76.5–76.9, 78.02, 424/78.03, 405, 406, 10.3, 9.6; 106/162.1, 106/287.1, 287.13, 287.2, 287.25, 287.35
See application file for complete search history.

(56) References Cited

U.S. PATENT DOCUMENTS

| | | | |
|---|---|---|---|
| 3,355,392 A | 11/1967 | Cantor et al. | |
| 4,568,534 A | 2/1986 | Stier et al. | |
| 4,584,192 A | 4/1986 | Dell et al. | |
| 4,678,658 A | 7/1987 | Casey et al. | |
| 5,064,635 A | 11/1991 | Casey | |
| 5,154,917 A | 10/1992 | Ibrahim et al. | |
| 5,278,132 A | 1/1994 | Fisher et al. | |
| 5,547,662 A * | 8/1996 | Khan et al. | 424/78.03 |
| 5,753,244 A * | 5/1998 | Reynolds et al. | 424/401 |
| 5,763,412 A | 6/1998 | Kahn et al. | |
| 5,955,062 A * | 9/1999 | McEleney et al. | 424/59 |
| 5,997,891 A | 12/1999 | Fuerst et al. | |
| 6,007,797 A | 12/1999 | Bell et al. | |
| 6,106,854 A * | 8/2000 | Belfer et al. | 424/405 |
| 6,146,618 A | 11/2000 | Bell et al. | |
| 7,147,873 B2 * | 12/2006 | Scholz et al. | 424/672 |
| 2005/0155628 A1 | 7/2005 | Kilkenny et al. | |
| 2005/0191326 A1 * | 9/2005 | Melker | 424/401 |
| 2006/0293205 A1 | 12/2006 | Chung | |
| 2007/0254854 A1 | 11/2007 | Magallon et al. | |
| 2008/0060550 A1 * | 3/2008 | MacDonald et al. | 106/162.1 |

FOREIGN PATENT DOCUMENTS

| | | |
|---|---|---|
| EP | 0 420 713 B1 | 4/1991 |
| EP | 0 549 145 A1 | 6/1993 |
| EP | 1 044 686 A1 | 10/2000 |
| EP | 1 457 529 A2 | 9/2004 |
| FR | 2 594 000 | 8/1987 |
| GB | 2 050 829 A | 1/1981 |
| GB | 2 326 340 A | 12/1998 |
| JP | 2002-256291 A | 9/2002 |
| WO | WO 94/26233 A1 | 11/1994 |
| WO | WO 96/14826 A1 | 5/1996 |
| WO | WO 98/23255 A1 | 6/1998 |
| WO | WO 99/60089 A1 | 11/1999 |
| WO | WO 00/76558 A1 | 12/2000 |
| WO | WO 02/102150 A1 | 12/2002 |
| WO | WO 2004/031334 A2 | 4/2004 |
| WO | WO 2006/105191 A2 | 10/2006 |
| WO | WO 2006/105193 A2 | 10/2006 |
| WO | WO 2006/105260 A1 | 10/2006 |
| WO | WO 2006/105261 A1 | 10/2006 |
| WO | WO 2007/008389 A2 | 1/2007 |
| WO | WO 2007/130982 A2 | 11/2007 |

OTHER PUBLICATIONS

Database WPI Week 200272 Thomson Scientific, London, GB; AN 2002-671628; XP002528724; Sep. 11, 2002.

* cited by examiner

*Primary Examiner* — Michael G Hartley
*Assistant Examiner* — Jagadishwar Samala
(74) *Attorney, Agent, or Firm* — Arent Fox LLP

(57) ABSTRACT

This invention discloses a surgical prep solution formulation, either film forming or non-film forming, that changes color upon a change in pH to indicate that the solvent has sufficiently evaporated. The major components of this surgical prep solution include: antimicrobial agents, solvents, pH adjusters, color changing pH indicators, and optionally: film forming polymers, dyes and viscosity regulators. The pH of the solution may rise or fall depending on the pH of the original solution as compared with the normal pH range of the acid mantle of the human skin or the normal pH range of a sterilizing solution. As the pH changes, the pH indicator may cause the surgical prep solution to change color. Concurrently, as the fluids evaporate, the pH indicators interact with atmospheric $CO_2$, causing the solution to change color based on the pH of the solution. The solution may also be used as coating for medical devices.

9 Claims, No Drawings

COLOR CHANGE SURGICAL PREP SOLUTION

FIELD OF THE INVENTION

This application is a Divisional Application which claims the benefit of U.S. patent application Ser. No. 11/542,791, filed Oct. 3, 2006,the disclosure of which is hereby incorporated in its entirety by reference.

BACKGROUND OF THE INVENTION

Pre-operative preparation of the skin with a topical antimicrobial agent is necessary to reduce the likelihood that the patient will contract a hospital-acquired infection during a surgery or surgical procedure. Typically, the healthcare practitioners, for example, prep nurses, apply a topical antimicrobial agent to a surgical or needle entry site before the procedure. Similarly, it is essential that medical devices that breach the skin be disinfected prior to penetrating the skin at an entry site or accessing an intravenous system. Healthcare practitioners typically disinfect these medical devices by applying an antimicrobial solution, e.g., alcohol, prior to use. Such treatment reduces the infection rate at the site or within the blood stream by hindering the growth of microorganisms or disinfecting a wound, surgical incision, or needle puncture site.

The human skin is normally covered with microorganisms such as bacteria, fungi, and viruses. The microorganisms are either transient, found on the skin's surface or are resident in deeper areas of the skin, such as the hair follicles.

The microorganisms are prevented from entering the body by the physical barrier of skin and the acid mantle, a protective layer formed by the mixture of sweat and sebum. The acid mantle maintains a moderately acidic covering for the normal human skin. The pH means and ranges for the normal skin of both adults and neonates are $5.7\pm0.16$ (range: 4.5-6.7) and $7.08\pm0.17$ (range: 6.6-7.5), respectively.

The function of the acid mantle is not completely understood even though the acidic environment of the skin's surface has been recognized for a century. However, the acid mantle is believed to assist the body in processing the lipids required for the skin to function as a barrier. Acidic environments also generally hinder bacterial growth, and hence, help resist bacterial infection.

Potential pathogens usually cannot enter the body if the skin and acid mantle remain intact. However, the integrity of the skin barrier is breached during surgical procedures, potentially exposing the surgical site or wound to microorganisms, increasing a patient's risk of infection. Thus, standard surgical procedures require that the skin at the surgical site be disinfected prior to surgery to reduce the patient's risk of infection. Therefore, there is a need in the art for a topical agent that will both kill the transient and resident microorganisms quickly and provide sustained antimicrobial activity throughout the entire surgery or surgical procedure.

Healthcare practitioners have long used ethanol or isopropanol, either alone or as a solvent along with other antimicrobial agents, to disinfect the skin at the surgical incision or needle puncture site and medical devices that penetrate the skin since these alcohols quickly reduce the population of bacteria, fungi, and some viruses at the site. Alcohol also provides rapid and sustained antimicrobial activity when it is combined with antimicrobial agents. However, alcohol based surgical prep solutions are flammable and certain surgical procedures cannot begin until the alcohol is completely evaporated. Hospital fires have been caused by unevaporated flammable solvents within surgical prep solutions. For the patient's safety, it is critical that healthcare practitioners be able to determine whether the flammable solvents within surgical prep solutions are completely evaporated prior to initiating energized surgical procedures, for example, electrocautery.

Solvent evaporation in particular presents a major challenge for healthcare practitioners for several reasons. First, it is difficult to visually determine when a colorless solvent (e.g., alcohol) has sufficiently evaporated to begin surgery or the surgical procedure. Second, the healthcare practitioners will often physically touch the skin surface or the medical device with a glove to determine the level of dryness. However, if the skin or medical device is not dry when touched, such a touch may breach the applied prep solution and provide a pathway for microorganisms to enter the body through the skin or via the medical device. Thus, it is necessary and desirable for the healthcare practitioners to have an easy way to determine if a solvent within a surgical prep solution has completely evaporated from the surgical site or the medical device without touching the skin, the medical device, or the applied surgical prep solution.

An effective film forming polymer may also be added to the surgical prep solution to provide better adherence of the solution to the skin or the medical device. Film forming polymers are either water soluble or insoluble and most of the water insoluble films adhere poorly to the skin. Poor adherence is especially problematic in orthopedic surgery or surgical procedures in which patients are draped after the surgical prep solution has dried. If the surgical prep solution adheres poorly to the skin or is water soluble, the drape will typically fall off during the procedure, contaminating the sterile surgical environment and increasing the chance of a hospital-acquired infection.

U.S. Pat. No. 5,763,412 teaches a film-forming composition containing chlorhexidine gluconate. U.S. Pat. No. 5,547,662 (hereinafter "the '662 patent") is directed to a film-forming composition for preparation of a skin surface as a surgical site containing an antimicrobial agent and Dowicide A and D&C Red 17, which changes color from purple (wet) to red (dry), but does not teach color changes triggered by pH indicators. The disadvantages of the '662 patent include inter alia the particular combination is not applicable to antimicrobial with inherent color, such as iodine or iodophors and the color change is not reversible. In addition, U.S. Pat. No. 4,584,192 teaches chlorhexidine or its derivative, but does not disclose which chlorhexidine compound is suitable and has no visualization feature.

SUMMARY OF THE INVENTION

This invention discloses a surgical prep solution formulation, either film forming or non-film forming, that changes color upon drying to indicate when the surgical prep solution has completely dried. Advantageously, the surgeon can determine that a selected surface, such as a surgical site or a medical device, is dry and the solvent has evaporated by visual determination.

DETAILED DESCRIPTION OF THE INVENTION

The present description emphasizes certain embodiments of the invention, but is not meant to be comprehensive of the entire scope of the invention. The full scope of the invention is measured by the appended claims.

The surgical prep solution comprises: topically-acceptable solvent(s), pH adjuster(s), color changing pH indicator(s) and optionally: antimicrobial agent(s), film forming polymer(s), dye(s) and viscosity regulator(s). After the solution is applied on the skin, the fluid components evaporate and the color changing pH indicator(s) interact with the human skin. The pH of the residue of the solution may rise or fall if the pH of the original solution is different from the normal pH range of the acid mantle of the human skin. As the pH of the residual solution changes, the pH indicator in the surgical prep solution may cause the residue to change color. Similarly and concurrently, as the fluid evaporates, the color changing pH indicator(s) may interact with atmospheric $CO_2$, changing the pH of the solution because $CO_2$ is mildly acidic. As such, the color changes according to the color properties of the pH indicator as the solution becomes less basic or more acidic. The rate of color change may be synchronized with the rate of fluid evaporation through the selection of pH indicators and pH adjusters so that the color change is complete when the fluid is sufficiently evaporated. Additionally, different color dyes and pH indicators may be utilized, to provide for a particular desired color.

The term "topically-acceptable solvent" as used here is a fluid that is compatible with the other ingredients of the composition and is non-toxic when applied to human skin. Suitable solvents include, but are not limited to, water, alcohols, acetone, esters, chlorinated hydrocarbons and chlorofluorohydrocarbons. Preferred solvents include, but are not limited to, water, and/or isopropanol, ethanol and other alcohols.

The term "antimicrobial agent" as used here is a chemical, such as a compound or salt that destroys or inhibits the growth of microorganisms. The term "microorganisms" as used here includes, but is not limited to, bacteria, fungi, and viruses. The antimicrobial agent may be, but is not limited to, alcohols (e.g., ethanol, isopropanol), chlorhexidine (e.g., chlorhexidine digluconate (CHG), chlorhexidine diacetate, chlorhexidine dihydrochloride, gluconic acid), hexachlorophene, iodophors, povidone-iodine, iodine, para-chlorometaxylenol (PCMX), and triclosan. Desirably, the antimicrobial agent is present in a quantity sufficient to inhibit microbial growth on the surface of the skin.

The term "antimicrobial agent sensitive to the environmental pH" as used here is an antimicrobial agent whose stability is influenced by the ambient pH. The antimicrobial agent sensitive to the environmental pH is a subset of the antimicrobial agents described above and may include, but is not limited to, iodine, iodophor, chlorhexidine and its derivatives, such as chlorhexidine gluconate. For instance, iodine and iodophor are naturally acidic and may gradually lose their antimicrobial activity if the environmental pH is basic. If the selected pH indicator changes color in the higher pH range (e.g., bromocresol purple which is yellow at pH below 5.2 and violet above 6.8), the antimicrobial activity of the iodophor solution may last up to several hours once a pH adjuster is added and the environmental pH turns basic. In a preferred embodiment where a pH adjuster is used where the environmental pH is not stable for antimicrobial agents, the solution should be applied immediately after the pH adjuster is added. In a more preferred embodiment, the two different pH components: (a) pH adjuster and/or pH indicator and (b) antimicrobial agents may be separately contained and mixed in situ through devices such as a dual channel syringe.

The term "film forming polymer" as used here is a polymer that forms a film that coats a surface (e.g., the skin) upon drying of the solution. The film is intact, resists both blood and saline, and contains the antimicrobial agent. Such polymer may include, but is not limited to, polyvinyl acetate, polyvinyl alcohol, methacrylic acid-ethyl acrylate copolymer, vinylpyrrolidone-vinyl acetate copolymer, polyvinyl alcohol-polyethylene glycol graft copolymer, ethyl acrylate-methyl methacrylate copolymer, acrylic polymers such as Eudragit®, and polyacrylate copolymer.

The term "pH indicator" as used here is a compound that is added in trace amounts to the surgical prep solution to determine its pH by visual observation. The pH indicator changes color based on the pH of the surgical prep solution. Such pH indicators include, but are not limited to, bromophenol blue, bromothymol blue, bromocresol green, bromocresol purple, congo red, methyl orange, methyl red, methyl yellow, pentamethoxy, phenolphthalein, thymophthalein, p-naphtholbenzein, 4-nitrophenol, 3-nitrophenol, o-cresolphthalein, m-cresol red, thymol blue, m-cresol purple, phenol red, and mixtures thereof. The pH indicator may be separately contained and added in situ prior to application to the skin at the surgical site. In a preferred embodiment, the composition undergoes a visible color change upon a change in pH from greater than about 6.5 to between about 4.0 to about 5.5. Alternatively, in another preferred embodiment, the composition undergoes a visible color change upon a change in pH from less than about 3.0 to between about 4.0 to about 5.5. More preferably, the composition undergoes a visible color change upon a change in pH from less than about 4.5 to between about 4.5 to 5.5.

The term "color dye" as used here are commonly used dyes or pigments. Such color dyes include, but are not limited to, D&C dyes (Green #5, Green #8, Orange #4, Red #4, Red #17, Red #22, Red #28, Red #33, Violet #2, Yellow #8, Yellow #10, Yellow #11), FD&C dyes (Blue #1, Blue #2, Carmine, Emerald Green, Green #3, Red #3, Red #40, Yellow #5, Yellow #6) and mixtures thereof.

The term "pH adjuster" as used here is an acid, a base or a pH buffer. The pH adjuster is used to adjust the solution pH so that the solution pH falls within one extreme of the color spectrum of the selected pH indicator. The rate of color change is controlled by the pH adjuster (i.e., acid, base or pH buffer). For instance, if one selects bromothymol blue as the pH indicator which is yellow when pH is below 6 and blue when pH is above 7.6, a pH adjuster is needed to change the solution pH to either below 6 or above 7.6. Such acids include, but are not limited to, acetic acid, boric acid, carbonic acid, chromic acid, citric acid, lactic acid, diluted hydrochloric acid, tartaric acid, propionic acid, malic acid, diluted phosphoric acid and mixtures thereof. Such bases include, but are not limited to, ammonium hydroxide, ammonium carbonate, ethylamine, dimethylamine, glycine, methylamine, trimethylamine, diethanolamine, sodium bicarbonate, sodium borate, sodium hydroxide, hydrazine, monoethanolamine, potassium hydroxide, sodium phosphate dibasic, trolamine and mixtures thereof. The pH adjuster may also include pH buffer agents such as the Hydrion™ buffer mixture produced by Micro Essential Laboratory, Inc. (Brooklyn, N.Y.) which contains a powdery mixture of potassium phosphate monobasic and sodium phosphate dibasic. The pH adjuster may be separately contained and added in situ prior to application because some antimicrobial agents have a shorter shelf life depending on the pH of their environment.

In a preferred embodiment, the composition according to the present invention is a liquid solution with a viscosity similar to water and/or ethanol. Alternatively, the composition may take various physical forms such as creams, gels, lotions, emulsions, foams, and the like. Viscosity regulators may be used to control the viscosity and rheological properties of the composition according to the invention. Suitable viscosity regulators include, but are not limited to, polyethylene glycol, polyethylene glycol derivatives, ethyl cellulose, methoxycellulose, hydroxyethylcellulose, polyvinylpyrrolidone/vinyl acetate copolymer, and crosslinked pyrrolidone.

A preferred embodiment of the surgical prep solution includes compounds that provide a first color which visually indicates the skin area covered by the composition and a second color which gives a visual indication that the solvent has been substantially eliminated by evaporation. These compounds usually refer to pH indicators, but it may also be other colored ingredients in the formulation, such as an antimicrobial agent or film forming polymers, as they alter the overall color.

In an alternative embodiment, the color change surgical prep solution is applied to medical devices, for example, needle-free connectors and valves. Generally, devices used for needle-free intravenous administration include one or more needle-free connectors. Preferably, the needle-free connectors include central venous catheters capable of accessing a patient's bloodstream. The needle-free connectors may function as access ports to the patient's bloodstream and may be used for injecting medication or drawing blood samples. The needle-free devices are designed to reduce accidental needle punctures and exposure to potentially infectious blood samples by substituting needles with needle-less devices for intravenous administration. The needle-free valve opens and fluid may flow therethrough when a fitting, preferably a male luer fitting, is inserted into the valve through a valve port. The valve seals when the fitting is removed and prevents fluid flow through the valve thereafter. The valve may, for example, be activated by a luer lock syringe, a secondary intravenous administration device or other intravenous products. In general, healthcare practitioners disinfect the needle-free connectors and valves with alcohol prep pads immediately prior to use.

It is essential that these medical devices are thoroughly disinfected in order to reduce a patient's risk of infection. Preferably, the color change surgical prep solution has a pH different from that of medical devices (e.g., needle-free connectors). The color change surgical prep solution may be swabbed onto a medical device. The solution may interact with surfaces of the medical device along with atmospheric $CO_2$, resulting in a pH change. As such, the color may change according to the color properties of the pH indicator as the solution becomes less basic or more acidic. A healthcare practitioner may visually inspect the color of the medical device to determine whether the medical device has been thoroughly disinfected. The use of the color change surgical prep solution may allow healthcare practitioners to visually identify the disinfected area based on the color change.

In another alternative embodiment, the color change surgical prep solution may be applied as a coating onto medical devices. The coating may contain a pH buffer having a pH different from that of disinfecting solutions (e.g., alcohol) typically used in hospitals. As soon as the sterilizing solutions (e.g., alcohol) are applied to the coated medical devices, the solution (e.g., alcohol) may interact with the coating and cause a change in pH. Accordingly, the color may change based on the color properties of the pH indicator as the solution becomes less basic or more acidic. A healthcare practitioner may visually inspect the color of the medical devices to determine whether the medical device has been thoroughly disinfected.

Preferably, the interaction between and the coating and the disinfecting solution is reversible and that the coating returns to its original color once the disinfecting solution fully evaporates. The reversible color change may be utilized repeatedly. For example, a medical device, such as a needle-free connector, needs to be disinfected every time the device is used. During the period of use, a healthcare practitioner may access the same needle-free connector to inject medicaments or draw blood samples. The connector may be disinfected by a disinfecting solution and change color. Once the disinfecting solution has fully evaporated, the connector may return to its original color. The connector may be repeatedly disinfected by the disinfecting solution. A color change may occur every time the disinfecting solution is applied to the connector and the connector may return to its original color every time the disinfecting solution becomes fully evaporated.

The invention offers several advantages over the prior art. First, the invention applies to both film forming and non-film forming prep solutions whereas the prior art is directed to film-forming color change surgical prep solutions.

Second, the prior art excludes antimicrobial agents with inherent color. For instance, the inclusion of iodine would render ineffective the color change abilities of the surgical prep solutions of the prior art. The invention overcomes such a limitation, allowing flexibility in choice of antimicrobial agents.

Third, the invention allows flexibility in the potential skin hues of patients. No two skin hues are the same and patients themselves might have variations of skin tone or even a colored tattoo. Thus, color flexibility in the surgical prep solution is imperative. In the invention, the color possibilities are more flexible than the prior art allows and hence, the surgical prep solution's color may be tailored to the needs of both patient and surgeon.

Fourth, for embodiments of the invention that include a film-forming polymer, the tinted color is embedded within the film and cannot easily be washed off because the film strongly adheres to the skin. This feature is especially important for orthopedic surgeons employing drapes on the patient.

Fifth, the invention reduces the risk of flammability. Surgeons regularly use electrocautery to burn or destroy tissue and hence, must be absolutely sure no flammable gases or liquids are present. Isopropanol is widely used as an antimicrobial agent, but it's flammability presents a problem to surgeons. The invention allows a surgeon to know when the isopropanol has been eliminated, thus reducing the risk of fire.

The invention also differs from the prior art in that pH indicators are used to change the color of the surgical prep solution. Known surgical prep solutions use chemicals such as Dowicide A and D&C Red 17 to change the color of the solution. Contrary to the present invention, the solvated Dowicide A and the dye form a complex and as the solvent evaporates, the complex shifts the wavelength of the light absorbed, thus changing the color of the complex. The mechanism is different from a pH-indicated color change.

The invention also differs from prior art in that the color change of the prep solution is reversible, if the environment pH change occurs during the procedure.

Finally, the invention facilitates the stability of antimicrobial agents that are unstable in certain pH ranges. The pH indicator and/or pH adjuster may be separately contained and added in situ prior to application to maintain the integrity of the antimicrobial agents and increase their effectiveness.

EXAMPLES

The following non-limiting examples illustrate particular embodiments of the invention. The examples are not meant to be comprehensive of the entire scope of the invention.

The following table lists both the composition of the one step surgical prep solution composition and a preferred embodiment.

| Ingredient | Amount (wt./wt. %) | Amount, preferred embodiment (wt./wt. %) |
| --- | --- | --- |
| Solvent | about 10-about 90 | about 60-about 80 |
| Antimicrobial agent (e.g. iodine or CHG, excluding alcohols) | about 0-about 5 | about 1.5-about 2.5 |
| Water | about 3-about 35 | about 15-about 25 |
| Color Dye (optional) | about 0-about 0.1 | about 0.005-about 0.05 |
| Film forming polymer (optional) | about 0-about 20 | about 0-about 10 |
| pH indicator | Trace | Trace |
| pH adjuster | Trace | Trace |
| Viscosity regulator | about 0-about 5 | about 0-about 5 |

In preparing the solutions, solid ingredients, such as polymers (including viscosity regulator), solvents, and color dye were first mixed to allow the slower-dissolving ingredients (i.e., film forming polymers, if used) time to dissolve in the solvent system. Afterwards, the antimicrobial agents were mixed in, followed by the pH indicator and pH adjuster. Each solution was mixed at room temperature using a magnetic stirring bar. These conditions apply to all the following examples.

If the antimicrobial agents are sensitive to pH, the pH adjuster and pH indicator may be initially separated and incorporated through devices such as a two-cylinder syringe with a static mixer or any other mixing mechanism and mixed with other components in situ prior to application.

Example A

Non-Film Forming

| Ingredient | Amount (wt./wt. %) |
| --- | --- |
| Isopropanol | 77.5 |
| Water | 20.5 |
| 0.1% Bromothymol blue in IPA | 1 |
| 1% Ammonium hydroxide | 1 |

In preparing the solution in Example A, isopropanol and water were mixed first. Subsequently, bromothymol blue was added and the solution pH was adjusted to between 8 to 10 using ammonium hydroxide. When applied to the skin, Example A changed from blue to light yellow/colorless after the solvent evaporated.

Example B

Non-Film Forming

| Ingredient | Amount (wt./wt. %) |
| --- | --- |
| Isopropanol | 64.2 |
| 20% CHG aqueous solution | 11.7 |
| Water | 22.05 |
| FD&C Red 40 | .05 |
| 0.1% Bromothymol blue in IPA | 1 |
| 1% Ammonium hydroxide | 1 |

In preparing the solution in Example B, Red 40, isopropanol, 20% CHG aqueous solution, and water were mixed first. Subsequently, bromothymol blue was added and the solution pH was adjusted to between 8 to 10 using ammonium hydroxide. When applied to the skin, Example B changed from purple to red after the solvent evaporated.

Example C

Non Film Forming

| Ingredient | Amount (wt./wt. %) |
| --- | --- |
| Isopropanol | 68.2 |
| 20% CHG aqueous solution | 8.5 |
| Water | 21.3 |
| 0.1% Bromothymol blue in IPA | 1.1 |
| 1% Ammonium hydroxide | 0.9 |

In preparing the solution in Example C, isopropanol, 20% CHG aqueous solution, and water were mixed first. Subsequently, bromothymol blue was added and the solution pH was adjusted to between 8 to 10 using ammonium hydroxide. When applied to the skin, Example C changed from blue to colorless after the solvent evaporated.

Example D

Film Forming

| Ingredient | Amount (wt./wt. %) |
| --- | --- |
| Polyacrylate copolymer | 7.4 |
| Isopropanol | 74.8 |
| Iodine | 0.68 |
| Sodium iodide | 0.62 |
| Water | 16.5 |
| Bromophenol blue | trace |
| Propionic acid | trace |

The components in Example D were combined to form a solution. Specifically, the polyacrylate was first dissolved in isopropanol and water, and then iodine, sodium iodide, and bromophenol blue were added. Propionic acid was used to adjust the solution pH to between 3.5 and 4. When applied on skin, the color changed from iodine gold color to green after the solvent evaporated. For this example, the integrity of the film was maintained for several hours and confirmed by visual observation.

Example E

Film Forming

| Ingredient | Amount (wt./wt. %) |
| --- | --- |
| Polyacrylate copolymer | 7.5 |
| Isopropanol | 74.9 |
| Water | 15.6 |
| CHG | 2.0 |
| FD&C Red 40 | 0.022 |
| Bromothymol blue | trace |
| Methylamine | trace |

In Example E, the polyacrylate copolymer and FD&C Red 40 were first dissolved in isopropanol and water. Subsequently, CHG and bromothymol blue were added and the solution pH was adjusted to between 8.5 and 9 using methylamine. When applied on skin, the color changed from purple to pink/red after the solvent evaporated. For this example, the integrity of the film was maintained for several hours and confirmed by visual observation.

Comparative Time-Kill Study

Examples F-I

The following Examples F-I were made to assess the formulation's antimicrobial effectiveness when dry.

Bacterial suspensions of *Escherichia coli* ATCC #11229 and *Staphylococcus aureus*, ATCC #6538 were made in sterile saline to final inoculum level of $1.5 \times 10^8$ CFU/ml. Thirty (30) microliters of the testing antimicrobial solution were aseptically spread on a sterile microslide covering a surface of 25×25 sq. mm and dried for ten (10) minutes. One (1) microliter of the microbial suspensions was applied on a sterile cover slip. The antimicrobial films were applied to these microbial suspensions for exposure times of 1, 5, or 10 minutes. After the exposure time had elapsed, both the cover slip and the micro slide were dropped into a test tube containing 10 ml sterile neutralizing solution. The Standard Plate Count Method was used for enumeration of the survival cells (CFU/ml). The log reduction in bacterial count was calculated from the log of the inoculum titers, which were enumerated by following the same procedure except without the presence of antimicrobial films.

Examples F-I present the results of the Time-Kill Study with the respective film solution.

Example F

Antimicrobial Efficacy

| Ingredient | Amount (wt./wt. %) |
| --- | --- |
| Film forming polymer | 7.37 |
| Iodine | 0.67 |
| Sodium iodide | 0.71 |
| Isopropanol | 73.69 |
| Water | 16.38 |
| Formic acid | 1.16 |
| Bromophenol blue | 0.02 |

In preparing the solution in Example F, the film forming polymer was first dissolved in isopropanol and water. Afterwards, iodine, sodium iodide and bromophenol blue were added. The final pH was then adjusted to between 3.5 to 4 using formic acid.

| Microorganism tested | Storage time at ambient conditions | Log reduction/ml at time intervals | | |
| --- | --- | --- | --- | --- |
| | | 1 min. | 5 min. | 10 min. |
| *E. coli*, gram negative bacterium | 0 time | >4.98 | >4.98 | N/A |
| | 2 week | >5.04 | >5.04 | N/A |
| | 1 month | >4.86 | >4.86 | >4.86 |
| | 2 months | >5.05 | >5.05 | >5.05 |
| *S. aureus*, gram positive bacterium | 0 time | 1.25 | 4.56 | N/A |
| | 2 week | 1.21 | 3.92 | N/A |
| | 1 month | 2.21 | >4.62 | >4.62 |
| | 2 months | 4.29 | >5.49 | >5.49 |

Example G

Antimicrobial Efficacy

| Ingredient | Amount (wt./wt. %) |
| --- | --- |
| Film forming polymer | 7.42 |
| Iodine | 0.68 |
| Sodium iodide | 0.72 |
| Isopropanol | 74.17 |
| Water | 16.49 |
| Formic acid | 0.5 |
| Bromophenol blue | 0.02 |

In preparing the solution in Example G, the film forming polymer was first dissolved in isopropanol and water. Afterwards, iodine, sodium iodide, and bromophenol blue were added. The final pH was then adjusted to between 3.5 to 4 using formic acid.

| Microorganism tested | Storage time at ambient conditions | Log reduction/ml at time intervals | | |
| --- | --- | --- | --- | --- |
| | | 1 min. | 5 min. | 10 min. |
| *E. coli*, gram negative bacterium | 0 time | >5 | >5 | N/A |
| | 2 week | 3.72 | >5.04 | N/A |
| | 1 month | 4.01 | >4.86 | >4.86 |
| | 2 months | >5.05 | >5.05 | >5.05 |
| *S. aureus*, gram positive bacterium | 0 time | >4.75 | >4.75 | N/A |
| | 2 week | 1.45 | >5.07 | N/A |
| | 1 month | 2.09 | >4.62 | >4.62 |
| | 2 months | 5.01 | >5.49 | >5.49 |

Example H

Antimicrobial Efficacy

| Ingredient | Amount (wt./wt.) |
| --- | --- |
| Film forming polymer | 7.40 |
| Iodine | 0.68 |
| Sodium iodide | 0.70 |
| Isopropanol | 74.64 |
| Water | 16.45 |
| Formic acid | 0.03 |
| Citric acid, anhydrous | 0.08 |
| Bromophenol blue | 0.02 |

In preparing the solution in Example H, the film forming polymer was first dissolved in isopropanol and water. Afterwards, iodine, sodium iodide and bromophenol blue were added. The final pH was then adjusted to between 3.5 to 4 using both citric acid and formic acid.

| Microorganism tested | Storage time at ambient conditions | Log reduction/ml at time intervals | | |
| --- | --- | --- | --- | --- |
| | | 1 min. | 5 min. | 10 min. |
| *E. coli*, gram negative bacterium | 1 month | >5.05 | >5.05 | >5.05 |
| *S. aureus*, gram positive bacterium | 1 month | 4.13 | >5.49 | >5.49 |

Example I

Antimicrobial Efficacy

| Ingredient | Amount (wt./wt.) |
| --- | --- |
| Film forming polymer | 7.29 |
| Iodine | 0.67 |
| Sodium iodide | 0.62 |
| Isopropanol | 74.79 |
| Water | 16.20 |
| Propionic acid, 99.5% | 0.31 |
| Citric acid, anhydrous | 0.10 |
| Bromophenol blue | 0.02 |

In preparing the solution in Example I, the film forming polymer was first dissolved in isopropanol and water. Afterwards, iodine, sodium iodide and bromophenol blue were added. The final pH was then adjusted to between 3.5 to 4 using both citric acid and propionic acid.

| Microorganism tested | Storage time at ambient conditions | Log reduction/ml at time intervals | | |
| --- | --- | --- | --- | --- |
| | | 1 min. | 5 min. | 10 min. |
| *E. coli*, gram negative bacterium | 10 days | >5.05 | >5.05 | >5.05 |
| *S. aureus*, Gram positive bacterium | 10 days | 4.38 | >5.49 | >5.49 |

Examples J-M

Rate of Color Change

Examples J-M illustrate the rate of color change controlled through different acid combinations. Specifically, the higher proportion of acid, the slower the color change when applied on skin.

| Ingredient (wt/wt %) | Example J | Example K |
| --- | --- | --- |
| Film forming polymer | 8.967 | 8.950 |
| Iodine | 0.727 | 0.726 |
| Sodium iodide | 0.777 | 0.776 |
| Isopropanol | 72.350 | 72.293 |
| Water | 16.937 | 16.907 |
| Citric acid | 0.157 | 0.263 |
| Formic acid | 0.060 | 0.060 |
| Bromophenol blue | 0.025 | 0.025 |

After being applied on skin, Example J changes color within 1 minute while Example K changes color within 2 to 3 minutes.

| Ingredient (wt/wt %) | Example L | Example M |
| --- | --- | --- |
| Film forming polymer | 7.43 | 7.43 |
| CHG | 2.00 | 2 |
| Isopropanol | 74.81 | 74.81 |
| Water | 15.63 | 15.63 |
| Bromothymol blue | 0.07 | 0.07 |
| Ammonium hydroxide | 0.06 | — |
| Dimethylamine | — | 0.06 |

After being applied on skin, Example L color changes from blue to colorless within 1 minute while it takes Example M more than 2 minutes to change color.

What is claimed is:

1. A method of disinfecting comprising:
providing a composition comprising an an antomicrobial agent and either: (a) one or more pH adjusters or (b) a color-changing pH indicator;
when the composition comprises the color-changing pH indicator, adding the one or more pH adjusters to the composition in situ prior to application of the composition to a patient's skin;
when the composition comprises the one or more pH adjusters, adding the color-changing pH indicator to the composition in situ prior to application of the composition to the patient's skin;
applying the composition to the patient's skin;
evaporating the composition; and visually inspecting the residue of the composition on the patient's skin for a change in color,
wherein the one or more pH adjusters is an acid, a base, a pH buffer or a combination thereof, and
wherein the composition undergoes a visible color change between a pH of about 4.0 to about 5.5.

2. The method of claim 1,
wherein the one or more pH adjusters comprise an acid, a base, or a pH buffer,
wherein the add is selected from the group consisting of acetic acid, boric add, carbonic acid, chromic acid, citric acid, lactic acid, hydrochloric acid, tartaric acid, propionic acid, malic acid, phosphoric acid, and mixtures thereof,
wherein the base is selected from the group consisting of ammonium hydroxide, ammonium carbonate, ethylamine, dimethylamine, glycine, methylamine, trimethylamine, diethanolamine, sodium bicarbonate, sodium borate, sodium hydroxide, hydrazine, monoethanolamine, potassium hydroxide, sodium phosphate dibasic, trolamine and mixtures thereof.

3. A method of disinfecting comprising:
providing a composition comprising an antimicrobial agent, a topically-acceptable solvent, and either (a): one or more pH adjusters or (b) a color-changing pH indicator;
when the composition comprises the color-changing pH indicator, adding the one or more pH adjusters to the composition in situ prior to application of the composition to a patient's skin;
when the composition comprises the one or more pH adjusters, adding the color-changing pH indicator to the composition in situ prior to application of the composition to the patient's skin;
applying the composition to the patient's skin;
evaporating the composition; and
visually inspecting the residue of the composition on the patient's skin for a change in color,
wherein the one or more pH adjusters is an acid, a base, a pH buffer or a combination thereof, and
wherein the composition undergoes a visible color change between a pH of about 4.0 to about 5.5.

4. The method according to claim 3, wherein the antimicrobial agent is an antimicrobial agent sensitive to the environmental pH.

5. The method according to claim 4, wherein the antimicrobial agent sensitive to the environment pH is selected from the group consisting of iodine, idophor, chlorhexidine and chlorhexidine gluconate.

6. The method according to claim 3, further comprising preparing the composition of the applying step.

7. The method of claim 3,
wherein the one or more pH adjusters comprise an acid, a base, or a pH buffer,
wherein the acid is selected from the group consisting of acetic acid, boric acid, carbonic acid, chromic acid, citric acid, lactic acid, hydrochloric add, tartaric acid, propionic acid, myelic acid, phosphoric acid, and mixtures thereof, and
wherein the base is selected from the group consisting of ammonium hydroxide, ammonium carbonate, ethylamine, dimethylamine, glycine, methylamine, trimethylamine, diethanolamine, sodium bicarbonate, sodium borate, sodium hydroxide, hydrazine, monoethanolamine, potassium hydroxide, sodium phosphate dibasic, trolamine and mixtures thereof.

8. A method of disinfecting comprising:
coating a composition of a first color to a selected surface, the coating comprising one or more pH adjusters and a color-changing pH indicator,
applying a disinfecting solution to the selected surface,
visually inspecting the coating for a change in color to a second color;
evaporating the disinfecting solution; and
visually inspecting the coating for a change in color to the first color,
wherein the one or more pH adjusters is an acid, a base, a pH buffer or a combination thereof,
wherein the change in color to the first color occurs between a pH of about 4.0 to about 5.5.

9. The method of claim 8,
wherein the one or more pH adjusters comprise an acid, a base, or a pH buffer,
wherein the acid is selected from the group consisting of acetic acid, boric acid, carbonic acid, chromic acid, citric acid, lactic acid, hydrochloric acid, tartaric acid, propionic acid, malic acid, phosphoric acid and mixtures thereof, and
wherein the base is selected from the group consisting of ammonium hydroxide, ammonium carbonate, ethylamine, dimethylamine, giycine, methylamine, trimethylamine, diethanolamine, sodium bicarbonate, sodium borate, sodium hydroxide, hydrazine, monoethanolamine, potassium hydroxide, sodium phosphate dibasic, trolamine and mixtures thereof.

* * * * *